United States Patent
Marma et al.

(10) Patent No.: US 11,767,339 B2
(45) Date of Patent: Sep. 26, 2023

(54) SYNTHESIS OF REVERSIBLE NUCLEOTIDE TERMINATORS BY IN-SITU THIO-ALKYL GROUP TRANSFER FOR USE IN DNA SEQUENCING BY SYNTHESIS

(71) Applicant: Miltenyi Biotec B.V. & Co. KG, Bergisch Gladbach (DE)

(72) Inventors: Mong Sano Marma, Westborough, MA (US); Michel Perbost, Bergisch Gladbach (DE); Sameh Soliman, Bergisch Gladbach (DE); Xiao-Pei Guan, Bergisch Gladbach (DE)

(73) Assignee: Miltenyi Biotech B.V. & Co. KG, Bergisch Gladbach (DE)

( * ) Notice: Subject to any disclaimer, the term of this patent is extended or adjusted under 35 U.S.C. 154(b) by 71 days.

(21) Appl. No.: 17/574,610

(22) Filed: Jan. 13, 2022

(65) Prior Publication Data
US 2023/0014428 A1    Jan. 19, 2023

(51) Int. Cl.
C07H 1/00 (2006.01)
C07H 19/10 (2006.01)
C07H 19/20 (2006.01)

(52) U.S. Cl.
CPC ............. *C07H 1/00* (2013.01); *C07H 19/10* (2013.01); *C07H 19/20* (2013.01)

(58) Field of Classification Search
None
See application file for complete search history.

(56) References Cited

U.S. PATENT DOCUMENTS

| | | | | |
|---|---|---|---|---|
| 10,301,346 B2 * | 5/2019 | Marma | ................. | C07F 7/1804 |
| 10,336,785 B2 * | 7/2019 | Marma | ................. | C09B 23/166 |
| 2017/0211134 A1 | 7/2017 | Marma | | |
| 2019/0226018 A1 | 7/2019 | Luisa | | |

FOREIGN PATENT DOCUMENTS

WO    WO 2017/079498    5/2017

* cited by examiner

*Primary Examiner* — Traviss C McIntosh, III
(74) *Attorney, Agent, or Firm* — Jaquelin K. Spong

(57) ABSTRACT

The invention is directed to a method for production of a deoxynucleotide triphosphate according to general formula (7)

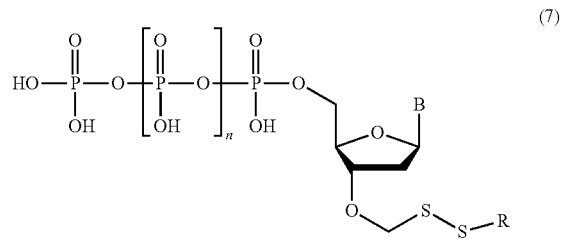

(7)

wherein B is a nucleobase and R is an alkyl group having 1 to 4 carbon atoms and n is an integer from 1 to 10 by reaction of reaction precursor of compound 6

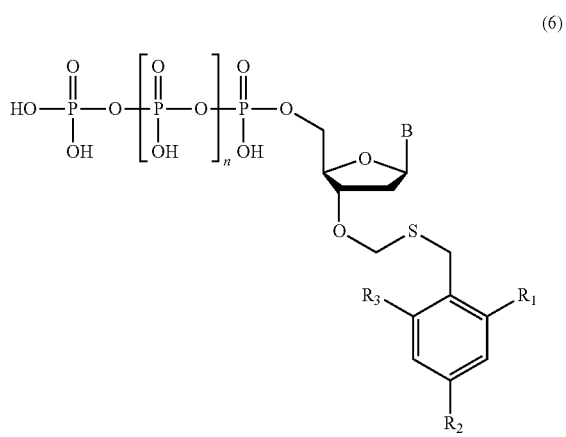

(6)

wherein $R_1$, $R_2$ and $R_3$ are independently H, O-Alkyl with alkyl residues having 1 to 4 carbon atoms or halogen and n is an integer from 1 to 10 with dialkyl(alkylthio) sulfonium salt (8B)

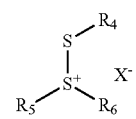

(8B)

wherein $R_4$, $R_5$, $R_6$ are independently alkyl residues having 1 to 4 carbon atoms and X is selected from the group consisting of $BF_4^-$, $F^-$, $Cl^-$, $Br^-$, $I^-$, $SO_4^{2-}$, $SO_3^{2-}$ in aqueous solution having a pH between 3 and 7.

6 Claims, 3 Drawing Sheets

SYNTHESIS OF REVERSIBLE NUCLEOTIDE TERMINATORS BY IN-SITU THIO-ALKYL GROUP TRANSFER FOR USE IN DNA SEQUENCING BY SYNTHESIS

CROSS REFERENCE TO RELATED APPLICATIONS

This U.S. nonprovisional application claims priority to EP21154663.5, filed Feb. 2, 2021. This prior application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

The present invention discloses a new process for upscale synthesis of reversible nucleotide terminators.

Next-generation DNA sequencing technology (NGS) is one of the key tools available in life sciences. It allows high throughput DNA sequencing. This technology is routinely used for genome sequencing, sequencing of multiple samples and multiple genes in a single experiment. In recent years, this technology has been the driving force for the rapid growth and advancement in the field of molecular diagnostics, precision medicines and synthetic biology, etc. Detailed reviews on current NGS technologies are provided by Jerzy K. Kulski, Next-generation sequencing—an overview of the history, tools, and "omic" applications, a book chapter in Next Generation Sequencing—Advances, Applications and Challenges, 2016, M. L. Metzker, Nature Reviews 2010, 11, 31, and C. W. Fuller et al., Nature Biotechnology 2009, 27, 1013.

At the core of the most widely used NGS technology is reversible nucleotide terminators. In standard construct of the reversible nucleotide terminators, the 3'-OH is capped with a chemically removable reversible group and each of the four bases is labeled by fluorescent dyes, attached via a cleavable linker. The nucleobase sequences in DNA is determined by enzymatic single base extension, followed by the detection of the fluorescently labeled nucleotides. The reversible nucleotide terminators are the key components of sequencing and the largest contributor to the cost of sequencing kits. The reason is the standard synthesis of them involves multiple step of reactions, purification and lyophilization at each step. Therefore for reducing the sequencing cost, the improvement of the manufacturing process of the nucleotides is essential.

SUMMARY

It was therefore an object of the invention to provide a method for production of a deoxynucleotide triphosphate according to general formula (7)

(7)

wherein B is a nucleobase and R is an alkyl group having 1 to 4 carbon atoms and n is an integer from 1 to 10 by reaction of reaction precursor of compound 6

(6)

wherein $R_1$, $R_2$ and $R_3$ are independently H, O-Alkyl with alkyl residues having 1 to 4 carbon atoms or halogen and n is an integer from 1 to 10 with dialkyl(alkylthio) sulfonium salt (8B)

(8B)

wherein $R_4$, $R_5$ $R_6$ are independently alkyl residues having 1 to 4 carbon atoms and X is selected from the group consisting of $BF_4^-$, $F^-$, $Cl^-$, $Br^-$, $I^-$, $SO_4^{2-}$, $SO_3^{2-}$ in aqueous solution having a pH between 3 and 7.

The method of the invention provides an ecofriendly way to obtain deoxynucleotide triphosphates according to general formula (7) in water solvent in acidic pH and optionally on crude intermediates i.e. without chromatographic purification).

The key to this method is in-situ introduction of the methyl-methylenedisulfide group (—$CH_2SSMe$) using trimethoxy-benzyl intermediate. This method allows upscale production of this class of reversible nucleotide terminators avoiding purification steps after triphosphorylation and hydrolysis of the protecting groups, and it is amenable to large scale synthesis. This new process removes a number of expensive purification steps as well as slow lyophilization steps in the synthesis of the said compounds and the overall yield has significantly increased.

The method of the invention comprises the use of DMTSF (Dimethyl(methylthio)sulfonium tetrafluoroborate) or its analogues (1) which acts as a donor of alkyl thiol group (RS$^+$, R=Me, Et etc). The RS$^+$ group replaces the substituted benzyl group from the nucleotide intermediate (3) forming 3'-O—CH$_2$SSR capped nucleotide as shown in scheme 1. When DMTSF is used (R=Me- in compound 1), it results in 3'-O—CH$_2$SSMe capped reversible nucleotide terminators (4) as shown in the scheme 1. We disclose herein a process where the introduction of —CH$_2$SSMe can be done on the crude product of compound 3—without requiring pre-purification.

Scheme 1: In-situ installation of 3'-OCH$_2$SSMe capping group in nucleotide synthesis. Crude product of compound 3 is treated with DMTSF in acetate buffer to converts to compound 4 without requiring pre-purification.

DMTSF, R = Me, and it's analogue (1)
R = alkyl, X = anionic counter ion, e.g. BF4$^-$ (2)
R1, R2, R3 = —OMe, H, —OEt, halogen etc
B = nucleobase - natural or non-natural (3)

(1, R = Me)    BF4$^-$    Acetate buffer, pH 4-6

(4)

DETAILED DESCRIPTION

The preparation of deoxynucleotide triphosphates according to general formula (7) is known and disclosed for example in the following patents: (1) Nucleotide analogues, patent number U.S. Ser. No. 10/301,346, filed: Nov. 4, 2016, date of patent: May 28, 2019. (2) Methods of using nucleotide analogues, patent number: U.S. Ser. No. 10/273,539, filed: Nov. 4, 2016, date of patent: Apr. 30, 2019, (3) Methods for synthesizing nucleotide analogues with disulfide linkers, patent number: U.S. Ser. No. 10/336,785, filed: Nov. 4, 2016, date of patent: Jul. 2, 2019.

In those patents, a new class of reversible nucleotide terminator is disclosed, where the 3'OH is capped with methyl-methylenedisulfide group (—CH$_2$SSMe) and cleavable linker with similar functional moiety (—OCH$_2$SS—C(Me)$_2$-, ref patent no. U.S. Ser. No. 10/301,346).

The capping group (—CH$_2$SSMe) is very unique—it is small but stable, which is essential for enzymatic incorporation and effective temporary termination. It is also labile enough to be enable us to remove under DNA compatible conditions. This functional group helps to temporarily stop the DNA synthesis by just single base incorporation but it can be resumed at will after chemical treatment when the capping group is removed. The cleavable linker, which has —OCH$_2$SS—C(Me)$_2$-moiety, as the capping group —OCH$_2$SSMe— a homologous structure, allowed us one step, single reaction cleaving off both the capping group and the fluorescent dyes.

Figure 1:
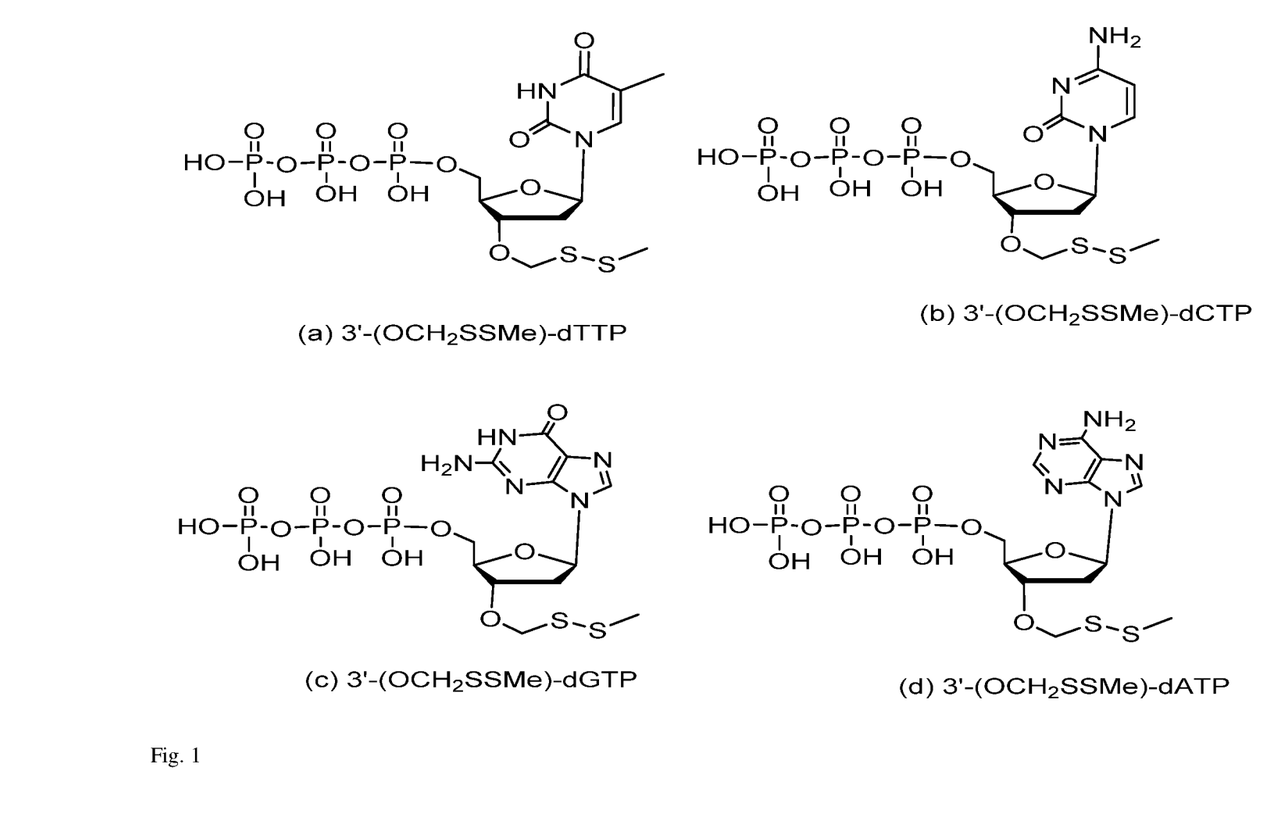
FIG. 1 shows a set of unlabeled (darks) reversible nucleotide terminators with 3'-OH capped by methyl-methylenemethyldisulfide (—CH2SSMe) groups
Figure 2:
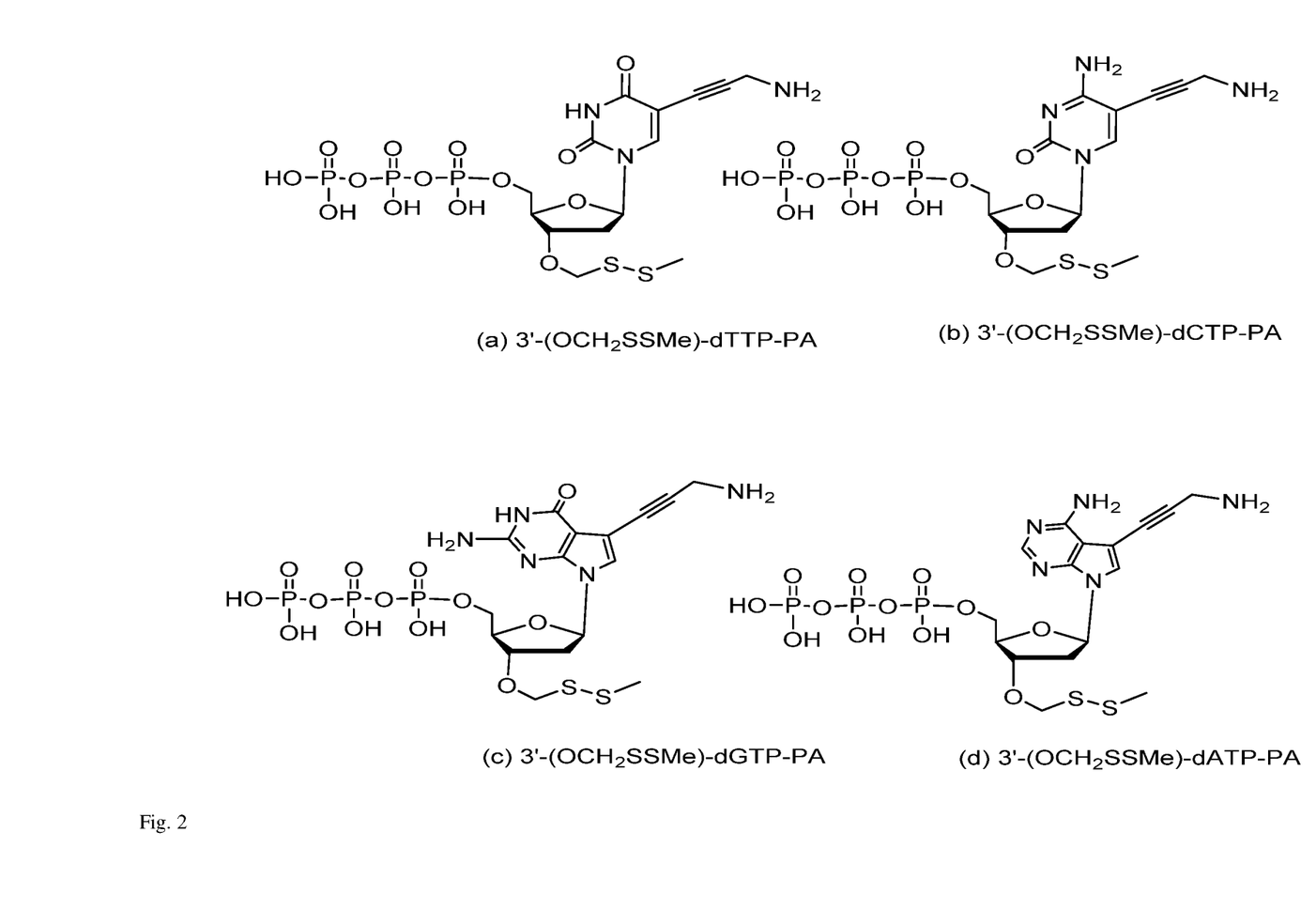
FIG. 2 shows a set of key intermediates with propargyl linker used for the synthesis of labeled reversible nucleotide terminators where the 3'-OH is capped by methyl-methylenedisulfide (—CH2SSMe). The nucleobases are modified by propargyl linker motif for attaching to the cleavable linker and fluorescent dyes or other reporter groups

In those patents, nucleotide constructs, composition and mix preparation are disclosed. This novel nucleotide enables us to develop a new generation four color DNA sequencing method on solid support. FIG. 1 shows structure of one set of unlabeled (dark) reversible nucleotide terminators, and FIG. 2 shows a set of key intermediates used for the synthesis of the labeled nucleotides shown in FIG. 3. All of them have one common function group that is the capping group on 3'-OH and a common cleavable linker. The synthesis of such nucleotides where 3'-OH group is capped with cleavable group such of —CH$_2$SSMe can be challenging due to labile nature of this group to certain reagents and conditions. It requires multiple step reactions, expensive purification and slow lyophilization steps.

In the preset invention, a way is disclosed, where a number of reactions are done sequentially on crude product obtained from the previous step eliminating purification steps, saving time, consumable materials such as purification columns and solvents, and importantly reactions are done environmentally friendly water solvent.

One key aspect of the new process disclosed here is using DMTSF (1) as thiomethyl transfer reagent and the substrate being compound 6 or its derivative obtained as crude (without pre-purification from prior steps). In this particular case the sensitive capping group —CH$_2$SSMe is introduced in-situ without requiring pre-purification of the crude product (6). The optimized process works smoothly at high concentration (~20.0 millimolar concentration) in acetate buffer at pH 4-6.0. The reaction needs only 2-3 equivalent of reagent—1, it is stunningly very fast reaction, usually completes in less than 10 minutes. This streamline method allows upscale production of reversible nucleotide terminators for next-generation DNA sequencing, cutting cost of production and the overall process time. Prior to the invention of this in-situ process, the overall process to obtain compound 7 involves multiple step of reaction, and the purification and lyophilization in each step, and reaction worked only on purified product at extremely high dilution (~1.0 millimolar concentration Vs ~20.0 millimolar concentration), requires too excessive reagent's equivalence (>30 equivalent Vs. ~2-3 equivalent) and lengthy reaction time—2-3 hours (Vs. ~10 mins) (Ref: patent number U.S. Ser. No. 10/336,785).

With this new process, the cost of production went down roughly 70%. This process can be employed universally to manufacture both the both darks shown in FIG. 1 and labeled nucleotide intermediates shown in FIG. 2.

Scheme 2

-continued (7)

Another aspect of this invention is generality of the use dimethyl(alkylthio) analogues (8) in acetate buffer with pH range 4-6 to produce 3'-O-alkyl-methylenedisulfide nucleotides (-3'-O—(CH$_2$SSR)dNTPs, scheme 3) group using thiobenzyl protected nucleotide triphosphates. The alkythiolating reagent is shown as 8, where R=Me, Et, t-But etc, X=BF$_4^-$ or other anionic counter ions such halogens (F$^-$, Cl$^-$, Br$^-$), —SO$_4^-$ etc. With this process, —CH$_2$SSEt, CH$_2$SSt-But etc protected nucleotides could be manufactured by similar in-situ mechanism disclosed above. Also, the general method for preparation of the alkylthiolating reagent 8 is perceived from alkyl-oxinium salt and methyldisulfide. The scheme 3 (b) shows how 3'-O—CH$_2$SSEt-dNTP could be prepared in situ-thioethylation.

Scheme 3

In another aspect, this invention comprises the use of 3'-OCH$_2$-thio-benzyl derivatives (9)

R$_1$, R$_2$, R$_3$=OMe, OEt, O-t-Bu as compound 9, where R$_1$, R$_2$, and R$_3$ are —OMe or other O-alkyl groups that stabilize the cationic benzyl leaving group in reaction cycle (e.g. —OEt, —OBut etc), B=natural or non-natural nucleobase or substituted molecule thereof. B can also be attached to a cleavable linker, and n=1-5.

In a first embodiment, B is nucleobase substituted with an alkyne group according to general formula (10) wherein R$_7$ is H or an straight chain or branched alkyl, alkene or alkyne group having 1 to 20 carbon atoms substituted or substituted with polyethylene glycol, —OH, —NH$_2$, —SH, —CO$_2$H, —CONH—.

(10)

(6)

In a second embodiment of the invention the reaction between reaction of precursor (6) and dialkyl(alkylthio) sulfonium salt (8B) takes place in aqueous solution having a pH between 4 and 7 in acetate buffer.

Figure 3:
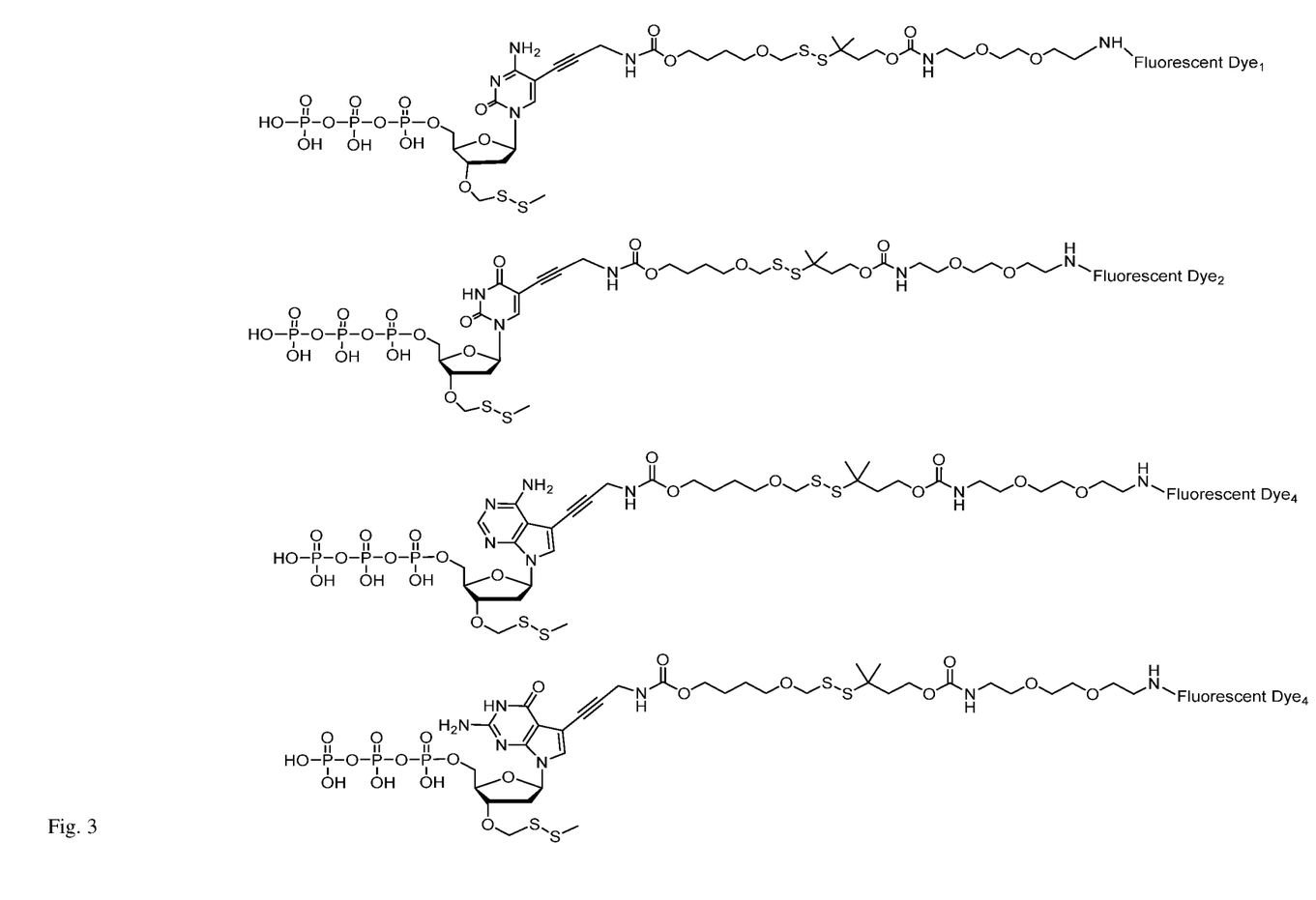
FIG. 3 shows a set of labeled reversible nucleotide terminators where the 3'-OH is capped by methyl-methylenedisulfide (—CH2SSMe). The nucleobases are attached to fluorescent dye reporters via a common cleavable oxymethylene disulfide linker (—OCH2SSCMe2-).

In a third embodiment, precursor (6) is obtained by phosphorylation of the 3'-O-benzylthiol nucleoside derivative (5), (5)

wherein B, $R_1$, $R_2$, $R_3$ have the same meaning as in formula (7) and (11) is used in the following reaction between reaction of precursor (6) and dialkyl(alkylthio)sulfonium salt (8B) without chromatographic purification. The overall reaction is shown in the following scheme In a forth embodiment of the method of the invention, deoxynucleotide triphosphate according to general formula (7) is provided with a nucleobase B which is substituted with an alkyne group and a cleavable group (CL) according to general formula (12)

wherein the cleavable linker (CL) contains at least one functional group selected from the group consisting of oxymethylenedisulfide (—OCH$_2$SSCMe$_2$-, —OCH$_2$SSCH$_2$—), oxymethinetrinitride (—OCHN$_3$—), disulfide (—SS—) and $R_8$ is a fluorescent dye. Preferred variants are shown in FIG. 3 The fluorescent dye is preferable a cyanine dye, rhodhamine dye, alexa dye, ATTO dye or their structural analogues.

EXAMPLES

With The 3'-O—CH$_2$SSMe capped nucleotide synthesis starts with 3'-OCH$_2$S-trimethoxybenzyl analogue (5). It is triphosphorylated by standard method such as Ludwig or Eckstein method and after removing all the protecting groups of the base by NH$_4$OH treatment, the volatile compounds and solvents are removed by lyophilization (or by high vacuum pump). It is then re-suspended in water and treat the crude product with DMTSF in acetate buffer in pH 4-6. The reaction is complete in 10 minutes. After neutralization with triethylamine to adjust pH 8.5, the crude can be stored at −20 degree freezer or immediately purified by ion-exchange chromatography resulting the desired product in ~25-40% yield.

This method allows production of the MeSSCH$_2$-capped reversible nucleotide terminators (MeSSdNTPs) in millimolar scale, and fully scalable to higher scale by linearly increasing reagents and solvent using standard laboratory equipment quickly cutting the cost of nucleotide production significantly. Synthesis of two classes of nucleotides with and without propargyl linker are discussed here, the latter compounds are key intermediates to the synthesis of fluorescently labeled reversible nucleotide terminators.

Here synthetic procedures of some representative compounds are described below Synthesis of 3'-OCH$_2$SSMe Capped dGTP, 3'-O—(CH$_2$SSMe)-dGTP, 12

-continued (12) 3'-O—(CH₂SSMe)-dGTP

In a 250 mL flask, 1.896 g (2.50 mmole) of 5'-OH-3'-O-(TMPMT)-dG (DPC)-Bu (10) was dried overnight under high vacuum in a desiccator in the presence of $P_2O_5$. It was dissolved by adding 4.0 mL dry pyridine and 7.0 mL 1,4-dioxane. The mixture was treated with 2-chloro-1,3,2-benzodioxaphosphorin-4-one (0.6 g, 2.96 mmole). The mixture was stirred at room temperature for 15 mins. A solution of tributylammonium pyrophosphate (1.8 g) was prepared by dissolving in 5.0 mL dry DMF and 1.8 mL $Bu_3N$ in a 50.0 mL centrifuge tube. The mixture was added to the rigorously stirred solution at once and resulting mixture was stirred for 10 minutes at room temperature. To the reaction mixture, $I_2$ (0.72 g, 2.84 mmole) solution, prepared in 5.0 mL pyridine and 0.5 mL HPLC grade water was added. The resulting mixture was stirred for 15 minutes. The excess iodine was then quenched by adding 1.0 mL of 5% $Na_2SO_3$ in HPLC grade water. After stirring for 5 minutes, the reaction was diluted with 80 mL HPLC grade water. The mixture was stirred for 1.5 hour at room temperature. The resultant solution was transferred to a 1,000 mL round bottom flask by decantation leaving behind the sticky—reddish precipitates. The mixture was treated with 240 mL of 28-30% $NH_4OH$, stirred for 24 hours at room temperature. The mixture was concentrated to dryness by lyophilization. The mixture was re-suspended in HPLC grade water and filtered to result in 120 mL crude filtrate solution of compound 11. The resultant crude product was diluted with 12 mL 3.0 M acetate buffer at pH 5.2. To rigorously stirring solution of this, 1.6 gm of dimethyl(methylthio)sulfonium fluoroborate (DMTSF, 8.2 mmole) was added and the mixture was stirred at room temperature for ~10 minutes. The resultant turbid mixture was neutralized with ~8.0 mL $Et_3N$ and precipitates were removed by centrifuge. The final product was obtained after ion-exchange purification on PL-SAX column (10μ, 1,000 A, 50×150 MM, Agilent, method: 0-5 min 100% A, followed by 80% B over 50 min, flow rate—40 mL/min; A=15% acetonitrile in HPLC grade water, B=15% acetonitrile in 0.85 M TEAB) followed by de-salting by flash chromatography on 275 g C18Aq Teledyne column resulted in 691 μmoles compound 3'-O—(CH2SSMe)-dGTP (12, 27.6% yield) after lyophilization and re-suspension in HPLC grade water (method: flow rate 80 mL/min, A=100 mM TEAB, B=acetonitrile, equilibration 15 min in 100% A, gradient method: 0-5 min 100% A, followed by 25% B over 5-45 min).

Synthesis of 3'-OCH2SSMe Capped dCTP, 3'-O—(CH₂SSMe)-dCTP (15)

Scheme 5: Triphosphorylation followed by in-situ installaton of 3'-O—CH₂SSMe capping group on dark C

(13)

(14)

(DMTSF) / Acetate buffer, pH 4-6

(15)

5′-OH-TMPMT-dC (Bz) 13 (3.1 g, 5.6 mmole) was transferred into a 250 mL round bottom flask. This flask, together with a magnetic stir bar and a rubber septum, were dried overnight under high vacuum in a desiccator in the presence of $P_2O_5$. It was dissolved in anhydrous pyridine (8.4 mL) and anhydrous 1,4-dioxane (16.8 mL), and was added partially crushed SalPCl solid (1.26 g, 6.2 mmole). The reaction mixture was stirred at room temperature for 30 minutes. A solution of tributylammonium pyrophosphate (3.8 g) in a mixture of $Bu_3N$ (3.9 mL) and anhydrous DMF (11.2 mL) was prepared in a 50 mL centrifuge tube. It was then added at once to the reaction mixture. The resulting reaction mixture was stirred at room temperature for 15 minutes. The product was oxidized by a solution of $I_2$ (1.56 g, 6.2 mmole) in pyridine (11.2 mL) and $H_2O$ (1.1 mL, HPLC grade). The resulting brown mixture was stirred at room temperature for 20 min. The excess $I_2$ was then quenched with 5% $Na_2SO_3$ (aq.) (2.3 mL). The mixture was stirred at room temperature for 5 min. The mixture was further diluted with $H_2O$ (147 mL). It was stirred at room temperature for another 1.5 hours at room temperature. The reaction mixture was then treated with $NH_4$—OH (28~30%, 110 mL). It was stirred at room temperature for 2 hours and complete de-protection was confirmed by HPLC and LCMS. The reaction mixture was lyophilized to dryness and the residue was re-suspended by HPLC grade water and filtered using a Corning filter system (0.22 μm). It was then transferred into a 250 mL bottle to give a crude TMPMT dCTP (14) solution in $H_2O$ (~100 mL). The solution of TMPMT-dCTP (14) in a 250 mL bottle was further diluted with $H_2O$ (90 mL), followed by the addition of acetate buffer (3.0 M, pH 5.2, 20 mL). To this mixture was added DMTSF solid (2.9 g) immediately. The resulting reaction mixture was stirred at room temperature for 20 minutes. The complete conversion was confirmed by HPLC. The reaction mixture was neutralized with triethylamine (8.4 mL) to pH 7.5 and then filtered using a Corning™ disposable bottle-top filter system (250 mL, CA 0.45 μm).

The reaction mixture was purified by ion-exchange HPLC on PL-SAX, 10 μm, 1000 Å, 50×150 mm (Agilent); Method: 0-2 min 100% A, then 80% B over 50 mins, flow rate 40 mL/min, A=ACN/water 15:85, B=ACN/1.0 M TEAB buffer 15:85). The column was regenerated with 5% AcOH/H2O and equilibrated with 100% A before injection. The target peak was collected and pooled together and lyophilized. The residue was dissolved in $H_2O$ (HPLC) & combined to give a crude product 15 solution ~2.4 mmol) in ~89% purity by HPLC. The crude product was de-salted by flash chromatography (Interchim PuriFlash—450; 275 g Redi Sep Rf Gold HP C18 Aq column; Method: 0-10 min 100% A, then 10% B over 30 mins; A=100 mM TEAB, B=ACN; flow rate 100 mL/min). The target fractions were combined and lyophilized. The product was dissolved in 1×TE buffer and combined to give the desired pure 3′-O—(CH2SSMe)-dCTP (15) in 1×TE. Total 90 mL (1,812 μmol, 36% from compound 13) in >99% purity by HPLC.

Synthesis of 3′-OCH$_2$SSMe Capped dTTP, 3′-O—(CH$_2$SSMe)-dTTP (18)

Scheme 6: Triphosphate synthesis by Eckstein method and in-situ 3′-O—CH$_2$SSMe - capping group installation of dark T In 250 mL round bottomed flask, 4.7 g (10.06 mmole) of 5′-OH-3′-(TMPMT)-dT (16) was dried overnight under high vacuum in the presence of P$_2$O$_5$ as a drying agent. It was dissolved in 15.0 mL dry pyridine and 30.0 mL dry 1,4-dioxane under nitrogen atmosphere. The mixture was treated with 2-chloro-1,3,2-benzodioxaphosphorin-4-one (2.294 g, 11.2 mmole) under nitrogen atmosphere. The mixture was stirred at room temperature for 30 mins. Then, a solution of tributylammonium pyrophosphate (7.0 g) in 20.0 mL dry DMF and 7.0 mL Bu$_3$N was prepared in a 50.0 mL centrifuge tube. The mixture was added at once and stirred for 10 minutes at room temperature. The reaction product was oxidized by a solution of I$_2$ (2.9 g, 11.4 mmole) in 20.0 mL pyridine and 2.0 mL HPLC grade water. The mixture was stirred for 15 minutes, turning into a reddish solution. The excess iodine was then quenched by adding 4.0 mL 5% Na$_2$SO$_3$ in HPLC grade water and stirred for 5 minutes. The reaction mixture was transferred into 1,000 mL flask and diluted with 300 mL of HPLC grade water. The clear solution was transferred to another new 1,000 mL by decantation leaving behind the red-brown precipitates.

The mixture was frozen initially on acetonitrile-dry ice bath (−40° C.) and later about 1.0 hour at −75° C. freezer, and lyophilized, which resulted in thick paste product. The product was re-suspended/extracted with HPLC grade water and the precipitates were removed by filtration and the total volume at this point is ~480 mL (crude stock ~21 mM 3′-(TMPMT)-dTTP, 17, based on starting material 16).

About half amount (~240 mL, ~5.0 mmole) of the 480 mL 3′-(TMPMT)-dTTP crude was taken in a different plastic bottle. It was diluted with ~30 mL 3.0 M acetate buffer pH 5.2. It was treated with 3.0 g of DMTSF and the mixture was stirred at room temperature for ~10 minutes. The HPLC of the mixture showed full conversion to MeSSdTTP (18). It's clear mixture (slight yellowish) was taken up into another flask after removing the precipitate by centrifugation (using 50 mL falcon tube). The mixture was adjusted to pH 7.0 by neutralizing with neat Et$_3$N (~15 mL). At this moment, total volume ~300.00 mL was split into two, each 150 mL (2.5 mmole). It was then purified by ion-exchange HPLC on PL-SAX (10 u, 1,000 A, 50×150 MM, Agilent), gradient: 0-5 min 100% A, followed by 80% B over 5-50 min, flow: 40 mL/min, A=15% ACN—H$_2$O, B=15% ACN-0.85M TEAB buffer, target peak with R$_f$=23-28 mins. The collected fractions were combined and lyophilized. The dried sample was re-suspended in 100 mM TEAB buffer and de-salted or final purified on C18 Sunfire column. yield: 780 umole, 31%, semi-pure product. Final purification/de-salting was carried on C18 Sunfire Waters Column (50×250 MM): Method: 0-2 min 100% A, then 40% B over mins, flow rate—40 mL/min, A=100 mM, B=ACN. Yield 607 umoles of compound 18 (~24% over all yield)

Synthesis of 3'-O—CH$_2$SSMe Capped dATP, 3'-O—(CH$_2$SSMe)-dATP (21)

Scheme 7: Triphosphate synthesis by Eckstein method and in-situ 3'O—CH$_2$SSMe capping group installation of dark A (19)

1.

pyridine, dioxane
2. Pyrophosphate-Bu$_3$N, Bu$_3$N, DMF
3. I$_2$-pyridine-H$_2$O
4. Na$_2$HSO$_3$—H$_2$O
5. NH$_4$OH (28-30%)—H$_2$O (20)

DMTSF | acetate buffer pH 5.2

-continued

(21)

In 250 mL pears-shaped flask, 1.454 g (2.50 mmole) of 5'-OH-3'-(TMPMT)-dA-Bz (19) was dried overnight under high vacuum in the presence of P$_2$O$_5$. It was dissolved by adding 4.0 mL anhydrous pyridine and 7.0 mL anhydrous 1,4-dioxane under nitrogen atmosphere. The mixture was treated with 2-chloro-1,3,2-benzodioxaphosphorin-4-one (0.6 g, 2.96 mmole) and the mixture was stirred at room temperature for 15 mins. A solution of Bu$_3$NH$^+$-pyrophosphate (1.8 g) in 5.0 mL dry DMF and 1.8 mL Bu$_3$N was prepared in a 50.0 mL centrifuge tube. The mixture was added at once and stirred for 10 minutes at room temperature. The product was then oxidized by adding a solution of I$_2$ (0.72 g, 2.84 mmole) prepared by dissolving in 5.0 mL pyridine and 0.5 mL HPLC grade water. The mixture was stirred for 15 minutes, turning into a reddish solution. The excess iodine was quenched by adding 1.0 mL of 5% Na$_2$SO$_3$ in HPLC grade water and stirred for 5 minutes. The mixture was diluted with 80 mL of HPLC grade water and was stirred for 1.5 hour at room temperature. The color of the mixture changed to a clear solution with red-sticky precipitations on the wall of the reaction flask. The clear solution was transferred to new 1,000 mL round bottom flask by decantation leaving behind the red precipitates. The mixture was treated with 240 mL of 28-30% NH$_4$OH for 8 hours. The product (20) was then lyophilized and the product was dissolved in HPLC grade water, resulting solution in ~100 mL (~25 mM apparent concentration, based on starting material amount). It was diluted with 12 mL 3.0 M acetate buffer pH 5.2 and treated with 1.6 g of DMTSF for 20 minutes. The resultant turbid mixture was neutralized with 6.0 mL Et$_3$N, precipitates were removed by centrifuge, the resulting pH ~9.0.

The product was purified by ion-exchange HPLC on PL-SAX column (10 u, 1,000 A, 50×150 MM, Agilent), HPLC gradient: 0-1 min 100% A, followed by 80% B over 50 min, flow rate: 40 mL/min, A=15% ACN—H$_2$O, B=15% ACN-0.85M TEAB buffer. Peak with R$_f$=25-30 mins was processed for lyophilization. After lyophilization, the product was further purified on 270 gm C18AQ column (Teledyne) by single injection, flow rate 80 mL/min, A=100 mM TEAB, B=acetonitrile, equilibration 15 min in 100% A, 0-5 min 100% A, then 25% B 5-40 min. All fraction was pulled together and lyophilized. The product 3'-O—(CH$_2$SSMe)-dATP (21) was dissolved in 1×TE and determined concentration by UV-spectrometry to yield total volume=60 mL, C=11.88 mM, yield=712 umoles (28.5% yield) in >98% purity.

Synthesis of 3'-OCH₂SSMe Capped dCTP-PA, 3'-O—(CH₂SSMe)-dCTP-PA (25)

Scheme 8: Thee starting material 5'-OH-3'-(TMPMT)-dC(N-Bz)-PA(COCF3) (22) is phosphorylated following Ecktein's triphosphorylation reaction to generate the intermediate product (23). Without any purification, the benzoyl protecting group (Bz) is removed from the nucleobase to generate product (24). Finally, the 3' protecting group is substituted with the desired group (MeSS-) to generate the final product (25).

MeSSdCTP-PA (25)

In a 250 mL pear shaped flask, 1.21 g (2.0 mmole) of 5'-OH-3'-(TMPMT)-dC(N-Bz)-PA(COCF3) (22) was dried overnight in a closed desicator under high vacuum (~7 mbar) in the presence of $P_2O_5$ as drying agent. It was dissolved by adding 5.0 mL dry pyridine and 9.0 mL dry 1,4-dioxane under nitrogen atmosphere. After 10 minutes stirring, it was found to be sparingly soluble, and it was then heated to 55 degree C. on a water bath and stirred to fully dissolve it and then the temperature of the flask was brought to room temperature on a water bath. When brought to the room temperature, the mixture was treated with 2-chloro-1,3,2-benzodioxaphosphorin-4-one (SalPCl, 0.486 g, 2.4 mmole) under nitrogen atmosphere (crush the larger crystals by a spatula before adding).

The mixture was stirred at room temperature for 15 mins under nitrogen atmosphere. A solution of $(Bu_3NH^+)_2$-pyrophosphate (1.44 g, 2.6 mmol) in 4.0 mL dry DMF and 1.44 mL $Bu_3N$ was prepared in a 50.0 mL centrifuge tube. The mixture was added at once and stirred for 10 minutes at room temperature. A solution of $I_2$ (0.64 g, 2.5 mmole) was prepared in 4.0 mL pyridine and 0.4 mL HPLC grade water. The mixture was added to the reaction. The mixture was stirred for 15 minutes, turning into a reddish solution. The excess iodine was quenched by adding 0.8 mL of 5% $Na_2SO_3$ in HPLC grade water and stirred for 5 minutes. and the mixture was diluted with 70 mL of HPLC grade water. The mixture was stirred for 1.0 hour at room temperature. The clear solution again was transferred to 1,000 mL round bottom flask leaving behind the sticky reddish precipitates on the bottom of the flask. The mixture was treated with 120 mL of 28-30% $NH_4OH$, stirred for 3 hours. The product was then lyophilized and the product was re-suspended in HPLC grade water, resulting a solution of 80 mL of crude compound 23. The solution was diluted with ~8.0 mL (10% V/V) of 3.0 M acetate buffer pH 5.2 (Sigma #S7899-500 mL). It was treated with 1.20 g of DMTSF and the mixture was stirred at room temperature for 10 minutes, which resulted in a brownish solution with reddish-grey precipitate sticky oil to the wall. Transferred to a bottle after filtration (0.22 µm CA, Corning, #430767). It was then neutralized with 3.0 mL $Et_3N$ to adjust pH ~8. The product was analyzed by HPLC: it shows a complete conversion to the expected 3'-O—$CH_2SSMe$ product (24). The crude was injected using a 20 mL syringe, for 2.0 mmoles a total of 5 successive injections were performed Product peaks with $R_f$=28-34 min was processed for lyophilization. After lyophilization, the product was re-suspended in HPLC grade water (~120 mL) to produce 3'-O—$(CH_2SSMe)$-dCTP-PA (25, 795 µmoles, 39% yield), measured by UV-Vis spectroscopy, $\lambda max$=293 nm, Emax=9,300 $Lmol^{-1}$ $cm^{-1}$.

What is claimed is:

1. A method for production of a deoxynucleotide triphosphate according to general formula (7)

wherein B is a nucleobase and R is an alkyl group having 1 to 4 carbon atoms and n is an integer from 1 to 10 by reaction of reaction precursor of compound 6 wherein $R_1$, $R_2$ and $R_3$ are independently H, O-Alkyl with alkyl residues having 1 to 4 carbon atoms or halogen and n is an integer from 1 to 10 with dialkyl(alkylthio)sulfonium salt (8B)

wherein $R_4$, $R_5$ $R_6$ are independently alkyl residues having 1 to 4 carbon atoms and X is selected from the group consisting of $BF_4^-$, $F^-$, $Cl^-$, $Br^-$, $I^-$, $SO_4^{2-}$, $SO_3^{2-}$ in aqueous solution having a pH between 3 and 7.

2. The method according to claim 1 characterized in that B is nucleobase substituted with an alkyne group according to general formula (10) wherein $R_7$ is H or an straight chain or branched alkyl, alkene or alkyne group having 1 to 20 carbon atoms substituted or substituted with polyethylene glycol, —OH, —NH$_2$, —SH, —CO$_2$H, —CONH—.

3. The method according to claim 1, characterized in that the reaction between reaction of precursor (6) and dialkyl (alkylthio)sulfonium salt (8B) takes place in aqueous solution having a pH between 4 and 7 in acetate buffer.

4. The method according to claim 1, characterized in that precursor (6) is obtained by phosphorylation of the 3'-O-benzylthiol nucleoside derivative (5), wherein B, $R_1$, $R_2$, $R_3$ have the same meaning as in formula (7) and (11) is used in the following reaction between reaction of precursor (6) and dialkyl(alkylthio) sulfonium salt (8B) without chromatographic purification.

5. The method according to claim 1, characterized in that B is nucleobase substituted with an alkyne group and a cleavable group (CL) according to general formula (12)

wherein the cleavable linker (CL) contains at least one functional group selected from the group consisting of oxymethylenedisulfide (—OCH$_2$SSCMe$_2$-, —OCH$_2$SSCH$_2$—), oxymethinetrinitride (—OCHN$_3$—), disulfide (—SS—) and $R_8$ is a fluorescent dye.

6. The method according to claim 5, characterized in that the fluorescent dye is a cyanine dye, rhodhamine dye, alexa dye, ATTO dye or their structural analogues.

* * * * *